(12) United States Patent
Chiu

(10) Patent No.: US 10,571,138 B2
(45) Date of Patent: Feb. 25, 2020

(54) HUMIDIFIER WITH REGULAR ADDITION OF FIXED QUANTITY OF ESSENTIAL OIL

(71) Applicant: Pao-Tien Chiu, New Taipei (TW)

(72) Inventor: Pao-Tien Chiu, New Taipei (TW)

(*) Notice: Subject to any disclaimer, the term of this patent is extended or adjusted under 35 U.S.C. 154(b) by 195 days.

(21) Appl. No.: 15/893,236

(22) Filed: Feb. 9, 2018

(65) Prior Publication Data
US 2019/0249888 A1    Aug. 15, 2019

(51) Int. Cl.
  *F24F 6/02* (2006.01)
  *A61L 9/14* (2006.01)
  *F24F 6/00* (2006.01)

(52) U.S. Cl.
  CPC .................. *F24F 6/02* (2013.01); *A61L 9/14* (2013.01); *A61L 2209/11* (2013.01); *F24F 2006/006* (2013.01)

(58) Field of Classification Search
  CPC . A61L 9/14; A61L 2209/11; F24F 6/02; F24F 2006/006
  USPC .................. 261/18.2, 30, 34.1, 37, 72.1, 81
  See application file for complete search history.

(56) References Cited

U.S. PATENT DOCUMENTS

| | | | | |
|---|---|---|---|---|
| 2,736,538 A * | 2/1956 | Barlow | ..................... | F01M 3/04 261/18.2 |
| 5,549,247 A * | 8/1996 | Rossman | .................. | A61L 9/14 239/338 |
| 6,786,474 B2 * | 9/2004 | Watkins | .................. | A61L 9/122 261/26 |
| 7,878,418 B2 * | 2/2011 | Sevy | ...................... | A61M 11/06 128/200.18 |
| 8,807,538 B2 * | 8/2014 | Sharma | ............... | A01M 1/2044 261/30 |
| 2002/0153622 A1 * | 10/2002 | Hugon | .................... | A61L 9/127 261/104 |

* cited by examiner

Primary Examiner — Charles S Bushey
(74) Attorney, Agent, or Firm — Muncy, Geissler, Olds & Lowe, P.C.

(57) ABSTRACT

A humidifier with regular addition of fixed quantity of essential oil is located in public areas and configured such that humidified air contains fragrance regularly. The humidifier is provided with a main body, water storage bucket mounted to the main body, and essential oil supplier mounted to the main body. The essential oil supplier includes a casing, at least one essential oil bottle within the casing and stored with essential oil, at least one peristaltic pump corresponding to each bottle and connected to the main body to be controlled. Each peristaltic pump is controlled by the main body, such that fixed quantity of essential oil is supplied regularly by the humidifier with the water storage bucket being not dismounted to keep fragrance in atomizing air continuous and eliminate the problem of only presence of fragrance at the beginning of addition of essential oil due to conventional method of addition.

6 Claims, 8 Drawing Sheets

HUMIDIFIER WITH REGULAR ADDITION OF FIXED QUANTITY OF ESSENTIAL OIL

FIELD OF THE INVENTION

The present invention is related to a humidifier, particularly to a humidifier with regular addition of fixed quantity of essential oil capable of being located in public areas.

BACKGROUND OF THE INVENTION

When the weather is cold, heaters are used in many public places or houses to improve room temperature. During the use of heaters, air is dried to cause discomfort. For this reason, humidifiers are used by many users while the heaters are turned on, so as to eliminate the problem of dry air via the humidifiers.

Recently, the addition of essential oil is desired by a part of users during the use of the humidifiers, so as to improve psychic state via fragrance generated by the essential oil. If the addition of essential oil in the humidifier is desired recently, however, it is only possible to drop essential oil into the atomization reaction zone without the water box being mounted to the humidifier such that essential oil is volatilized to generate fragrance while atomization reaction is performed in the humidifier. Nevertheless, the mass of essential oil is lower than that of water, such that the essential oil may float on water. In this way, the essential oil is volatilized rapidly, and thus the time period when mist contains fragrance may not meet expectations. Therefore, it is necessary for the user to disassemble and assemble the humidifier several times to keep mist containing fragrance continuously, which is truly inconvenient.

SUMMARY OF THE INVENTION

It is the main object of the present invention to solve the problem of incapability of keeping the time period, when mist contains fragrance, continuous, although essential oil may be added in the existing humidifier.

For achieving the above object, the present invention provides a humidifier with regular addition of fixed quantity of essential oil, the humidifier including a main body and a water storage bucket mounted to the main body, the main body being provided with a temporary liquid storage basin, an atomizing space defined by the temporary liquid storage basin, an atomizing plate located within the temporary liquid storage basin, a projecting stud located within the temporary liquid storage basin, a fan generating air stream within the atomizing space after being started, and a startup management module connected to the fan and the atomizing plate, a high water level line being defined on the temporary liquid storage basin, the water storage bucket being provided with a bucket body, a water supply switch provided on the bucket body and pushed by the projecting stud so as to permit water stored in the water storage bucket to flow into the temporary liquid storage basin, as well as an air guiding passage defined and formed by the bucket body while communicated to the atomizing space without being used for water storage. Further, the main body is provided with at least one essential oil delivering passage, corresponding to the temporary liquid storage basin, being located higher than the atomizing space and being communicated to the atomizing space, the humidifier being provided with an essential oil supplier mounted to the main body, the essential oil supplier including a casing, at least one essential oil bottle located within the casing and stored with an essential oil, at least one peristaltic pump corresponding to each essential oil bottle and being connected to the startup management module, the peristaltic pump being provided with a pump body, a peristaltic pump head connected to the pump body, and a liquid delivering hose connected to the peristaltic pump head, the liquid delivering hose being provided with a liquid supplying end connected to the essential oil delivering passage, and a liquid drawing end connected to the essential oil bottle.

In one embodiment, the casing is provided therein with a supporting panel, the supporting panel being openly provided with at least one mounting hole, the pump body and the peristaltic pump head of the peristaltic pump being located on two sides of the supporting panel, respectively, the pump body being connected to the peristaltic pump head through the mounting hole.

In one embodiment, the essential oil supplier is provided with a tube located at the end of the liquid delivering hose to be connected to the essential oil delivering passage.

In one embodiment, the bucket body includes an accommodating recess provided for the essential oil supplier to be selectively located therein without being prominently projected on the exterior of the water storage bucket.

In one embodiment, the main body includes a plurality of control switches connected to the startup management module and appeared at the outside of the main body.

In one embodiment, the main body is provided with a front side having the plurality of control switches, and a rear side having the essential oil supplier.

In comparison with the prior art, there are features, achieved by the disclosure mentioned above in the present invention, as follows. A fixed quantity of essential oil may be supplied regularly by means of the peristaltic pump in the present invention, such that fragrance may be kept continuous, not only presented during the first few minutes, in the process of supplying mist by the humidifier. In addition, it is further possible for a user to configure the structure of the present invention on the basis of usage habits and desired compound fragrance.

DETAILED DESCRIPTION OF THE PREFERRED EMBODIMENTS

Figure 1:
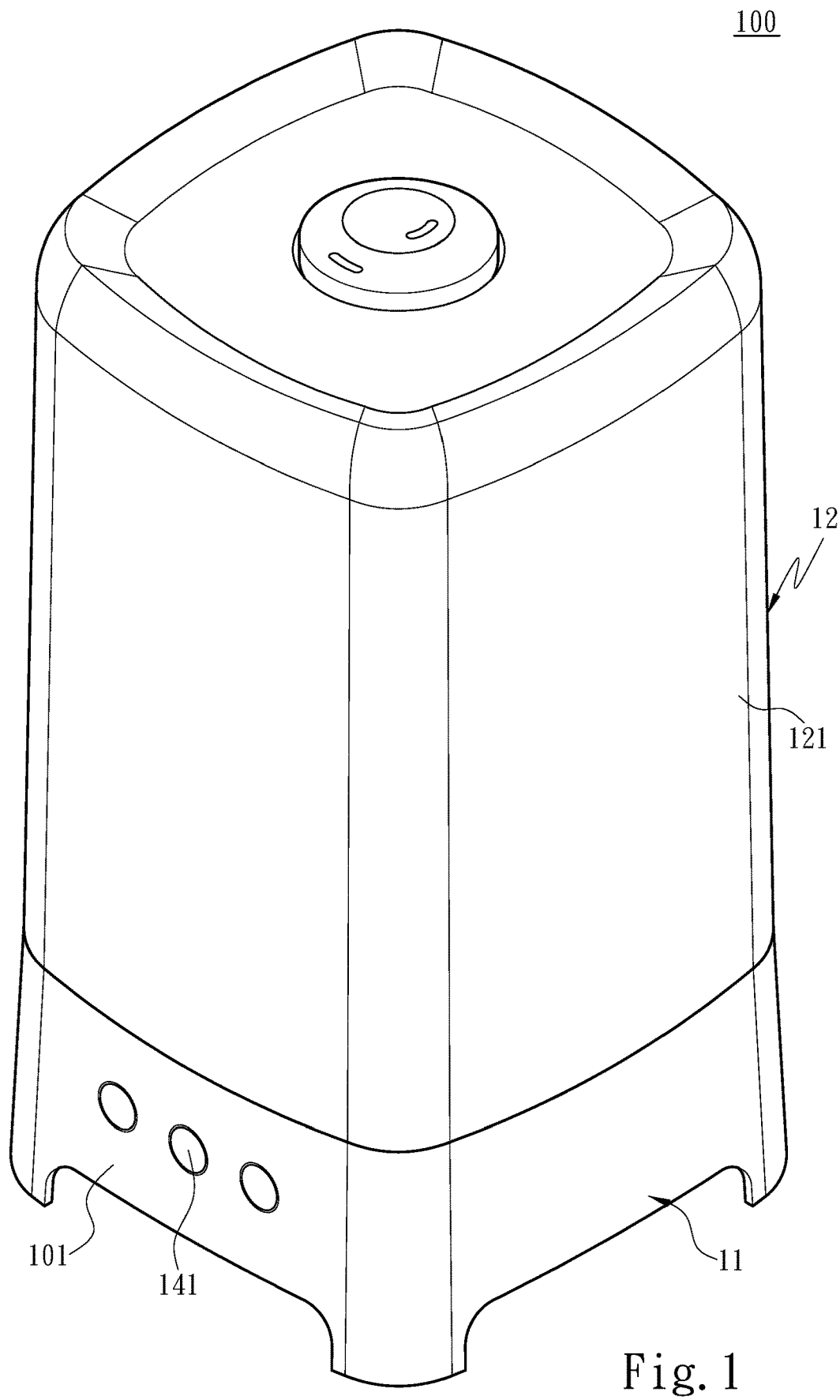
FIG. 1 is a structural view of one embodiment of the present invention.
Figure 2:
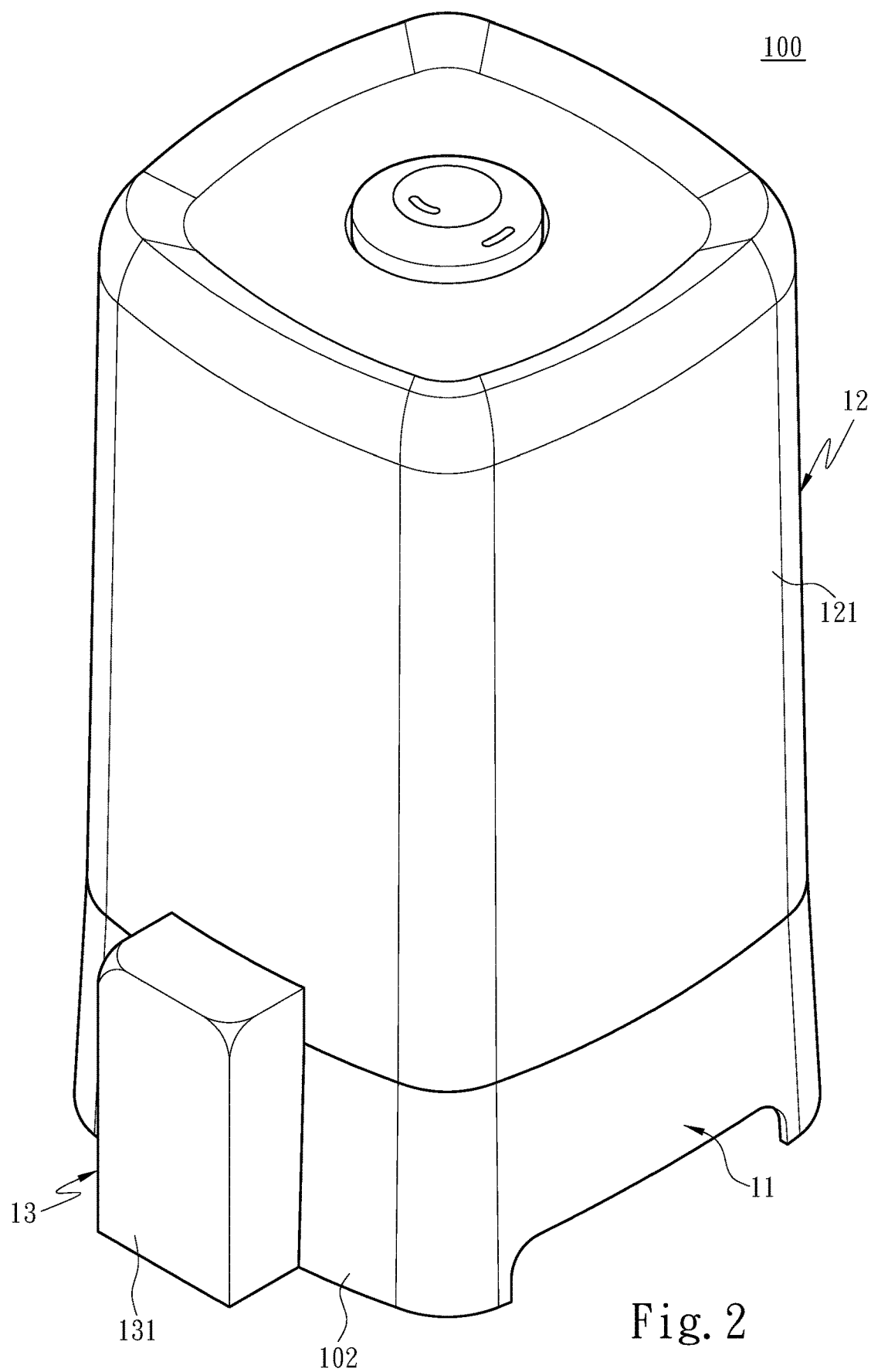
FIG. 2 is a structural view in another direction of one embodiment of the present invention.
Figure 3:
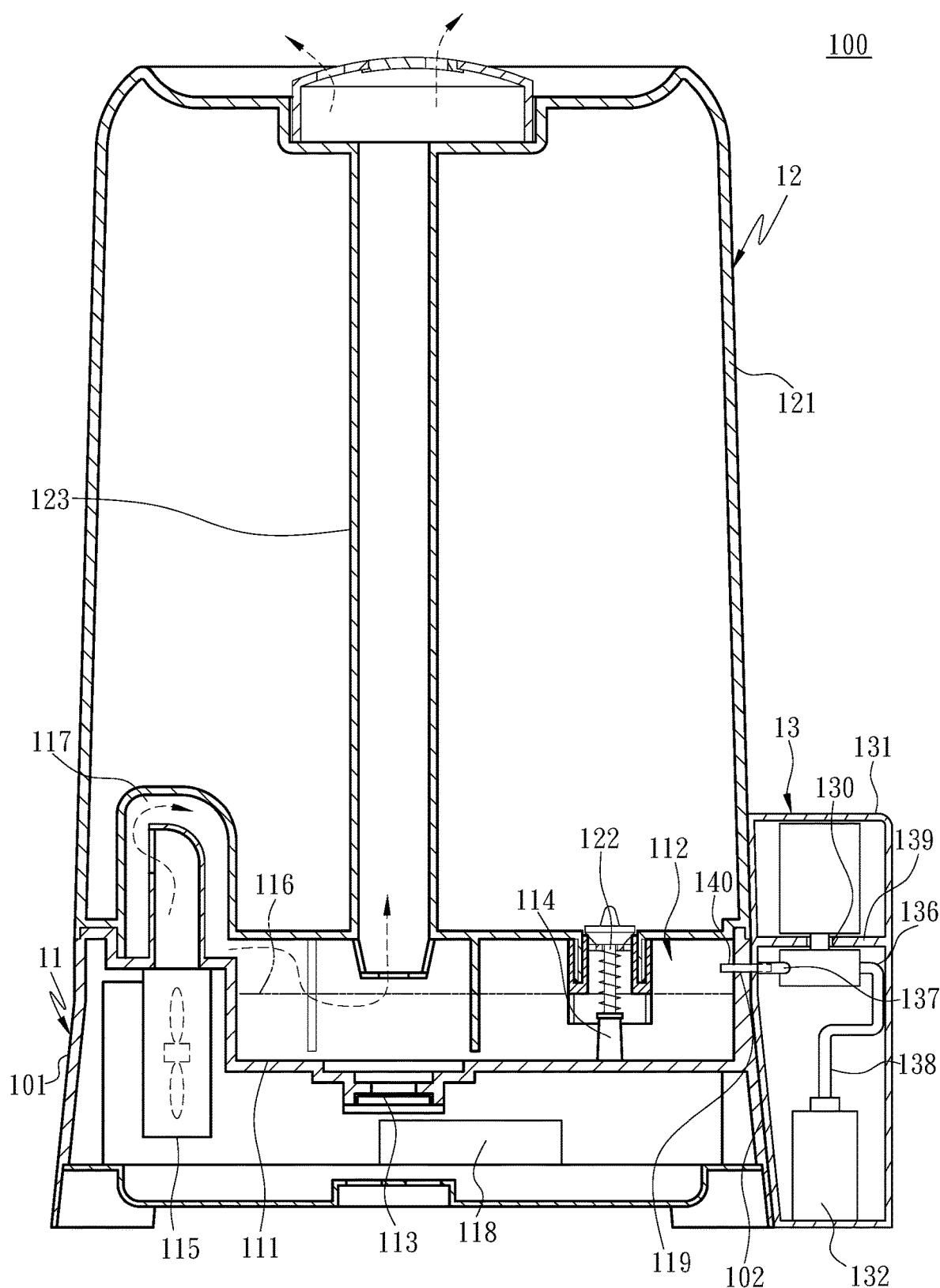
FIG. 3 is a structural cross-section view of one embodiment of the present invention.
Figure 4:
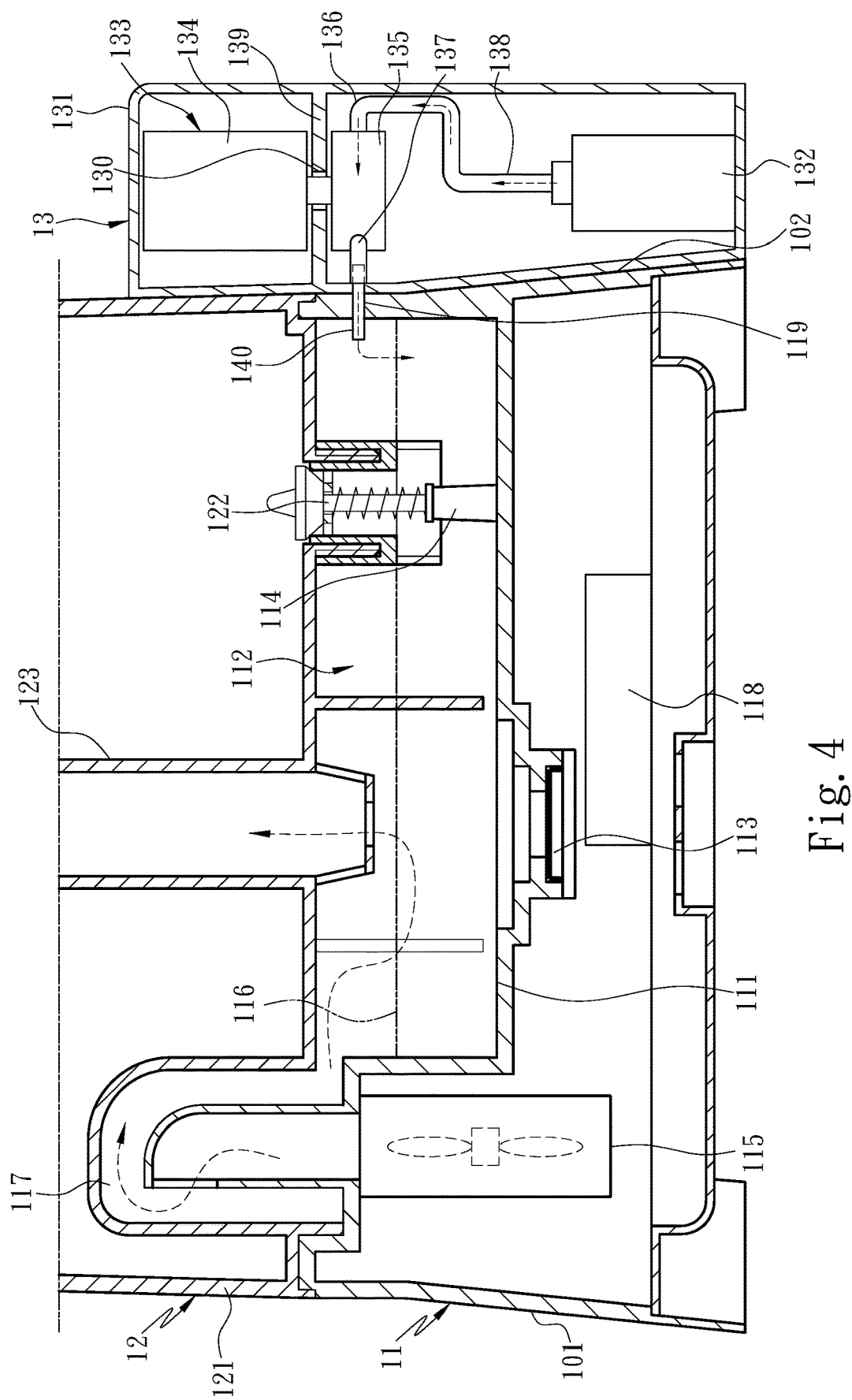
FIG. 4 is a locally structural cross-section view of one embodiment of the present invention.
Figure 5:
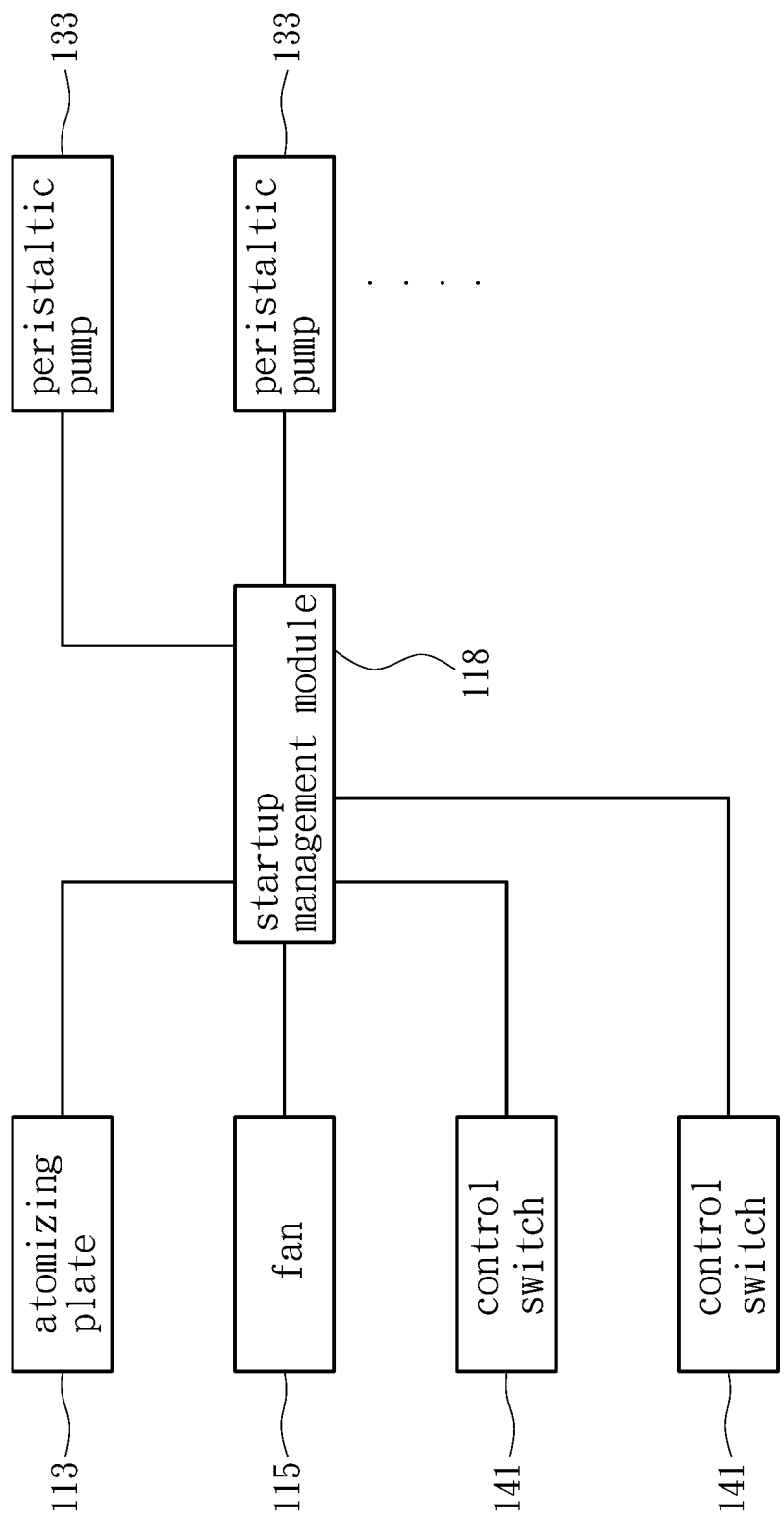
FIG. 5 is a component diagram of one embodiment of the present invention.

The detailed description and technical content of the present invention will be described, in conjunction with drawings, as follows.

Referring to FIG. 1, FIG. 2, FIG. 3, FIG. 4, and FIG. 5, the present invention provides a humidifier 100 with regular addition of fixed quantity of essential oil, the humidifier 100 being capable of being provided in a larger indoor space, such as a hotel lobby, department store or larger house. The humidifier 100 includes a main body 11 and a water storage bucket 12 mounted to the main body 11. The main body 11 is provided with a temporary liquid storage basin 111, an atomizing space 112 defined by the temporary liquid storage basin 111, an atomizing plate 113 located within the temporary liquid storage basin 111, a projecting stud 114 located within the temporary liquid storage basin 111, a fan 15 generating air stream within the atomizing space 112 after being started. More specifically, the water storage bucket 12 is mounted to the main body 11 at one side where the temporary liquid storage basin 111 is provided, as well as the water storage bucket 12 is capable of supplying the temporary liquid storage basin 111 with water and then allowing a little water being presented in the temporary liquid storage basin 111. Further, the pattern of the temporary liquid storage basin 111 is designed in according with the practical requirement without limitation herein. A high water level line 116 is defined on the temporary liquid storage basin 111, the high water level line 116 indicating a highest water level where pressure in the temporary liquid storage basin 111 and that in the bucket of the water storage bucket 12 are balanced when water is supplied to the temporary liquid storage basin 111 by the water storage bucket 12. Next, the atomizing plate 113 and the projecting stud 114 are provided at the bottom edge of the temporary liquid storage basin 111, respectively, and both of them are provided so as to face one end, which is open, of the temporary liquid storage basin 111. In addition, the main body 11 may be provided with an air stream passage 117 corresponding to the fan 115. The air stream passage 117 is provided at one end thereof on the air-exhaust side of the fan 115, while communicated at the other end thereof to the atomizing space 112. The air stream passage 117 is allowed to guide air stream into the atomizing space 112 when the fan 115 is started. Furthermore, the main body 11 is provided with a startup management module 118 connected to the fan 115 and the atomizing plate 113. The startup management module 118 mainly includes startup control and power supply.

In addition, the water storage bucket 12 is provided with a bucket body 121, a water supply switch 122 provided on the bucket body 121 and pushed by the projecting stud 114 so as to permit water stored in the water storage bucket 12 to flow into the temporary liquid storage basin 111, as well as an air guiding passage 123 defined and formed by the bucket body 121 while communicated to the atomizing space 112 without being used for water storage. Further, the bucket body 121 is configured to store at least one liter of water. The bucket body 121 may be generally annular with hollow center formed as the air guiding passage 123. Moreover, the water supply switch 122 is provided with a first state blocking water supply when the projecting stud 114 is not pushed, and a second state permitting water supply when the projecting stud 114 is pushed.

Furthermore, an essential oil delivering passage 119, corresponding to the temporary liquid storage basin 111, being located higher than the atomizing space 112 and being communicated to the atomizing space 112, is provided on the main body 11 in the present invention. The humidifier 100 is further provided with an essential oil supplier 13 mounted to the main body 11. The essential oil supplier 13 includes a casing 131, at least one essential oil bottle 132 located within the casing 131 and stored with an essential oil, at least one peristaltic pump 133 corresponding to each essential oil bottle 132 and being connected to the startup management module 118. The peristaltic pump 133 is provided with a pump body 134, a peristaltic pump head 135 connected to the pump body 134, and a liquid delivering hose 136 connected to the peristaltic pump head 135. The liquid delivering hose 136 is provided with a liquid supplying end 137 connected to the essential oil delivering passage 119, and a liquid drawing end 138 connected to the essential oil bottle 132. Further, the casing 131 is provided therein with a supporting panel 139. The supporting panel 139 is openly provided with at least one mounting hole 130. The pump body 134 and the peristaltic pump head 135 of the peristaltic pump 133 are located on two sides of the supporting panel 139, respectively. The pump body 134 is connected to the peristaltic pump head 135 through the mounting hole 130.

Referring to FIG. 4 again, when the present invention is put into practice, water stored in the water storage bucket 12 is flowed to the temporary liquid storage basin 111 via the water supply switch 122. When electric power supplied by the startup management module 118 is received by the atomizing plate 113, water stored in the temporary liquid storage basin 111 is transformed into mist by the atomizing plate 113, and meanwhile electric power supplied by the startup management module 118 is also received by the fan 115 to start this fan. Wind generated by the fan 115 is allowed for impelling mist toward the air guiding passage 123, and then mist is discharged through the air guiding passage 123 to humidify the neighborhood. In addition, when the addition of essential oil is desired in the present invention, it is unnecessary to dismount the water storage bucket 12. The peristaltic pump 133 is allowed for rotating the peristaltic pump head 135 to act on the liquid delivering hose 136 when electric power supplied by the startup management module 118 is received by this peristaltic pump. The essential oil within the essential oil bottle 132 is drawn through the liquid drawing end 138, and then guided into the essential oil delivering passage 119 through the liquid supplying end 137 by the liquid delivering hose 136. Afterwards, the essential oil is introduced into the temporary liquid storage basin 111 through the essential oil delivering passage 119. The essential oil will participate in atomization reaction, such that fragrance is added in mist. Additionally, the essential oil is supplied when the peristaltic pump 133 is started by the startup management module 118, and not supplied at one time in the present invention. Even if the peristaltic pump 133 is started over a long period of time, a fixed quantity of essential oil is supplied regularly by means of the peristaltic pump 133. As such, extremely quick volatilization of the essential oil and the resulted incapability of remaining fragrance in mist for a long time, due to the conventional one-off addition of the essential oil, may be avoided.

Figure 6:
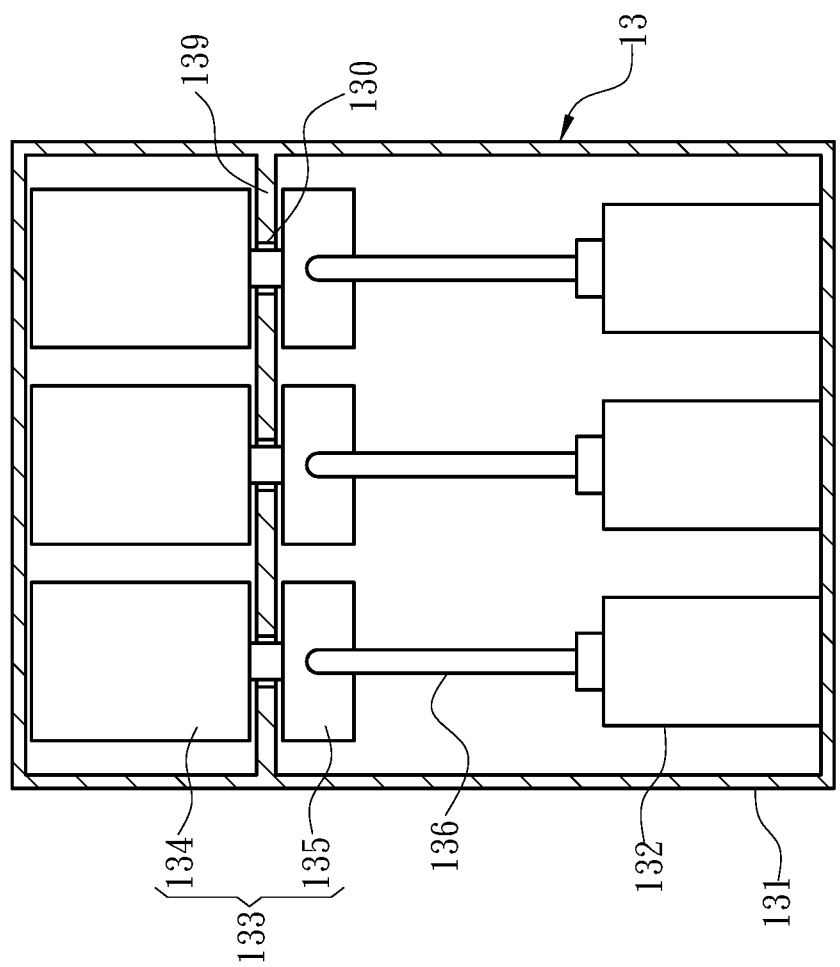
FIG. 6 is a structural view of an essential oil supplier of one embodiment of the present invention.

Besides, referring to FIG. 6 together, the essential oil supplier 13 of the present invention may be provided with a plurality of peristaltic pumps 133 and a plurality of essential oil bottles 132. The types of the essential oil stored within the essential oil bottles 132 may be different from each other. For instance, the lavender essential oil is stored in one of the essential oil bottles 132, while the tangerine essential oil is stored in another one of the essential oil bottles 132. Furthermore, the startup management module 118 may be provided for setting the startup time of each peristaltic pump 133, such that fragrance in mist may be varied on the basis of the time. Additionally, in this embodiment, the fragrance may be no longer one single odor, instead of the startup management module 118 may be configured on the basis of the compound to be implemented desirably, such that the corresponding peristaltic pumps 133 are started by the startup management module 118 on the basis of the compound.

Referring to FIG. 4 again, in one embodiment, the essential oil supplier 13 is provided with a tube 140 located at the end of the liquid delivering hose 136 to be connected to the essential oil delivering passage 119. The tube 140 may be made of metal or plastic, and the bore size of the tube 140 at one end thereof may be configured on the basis of the bore size of the liquid delivering hose 136.

Figure 7:
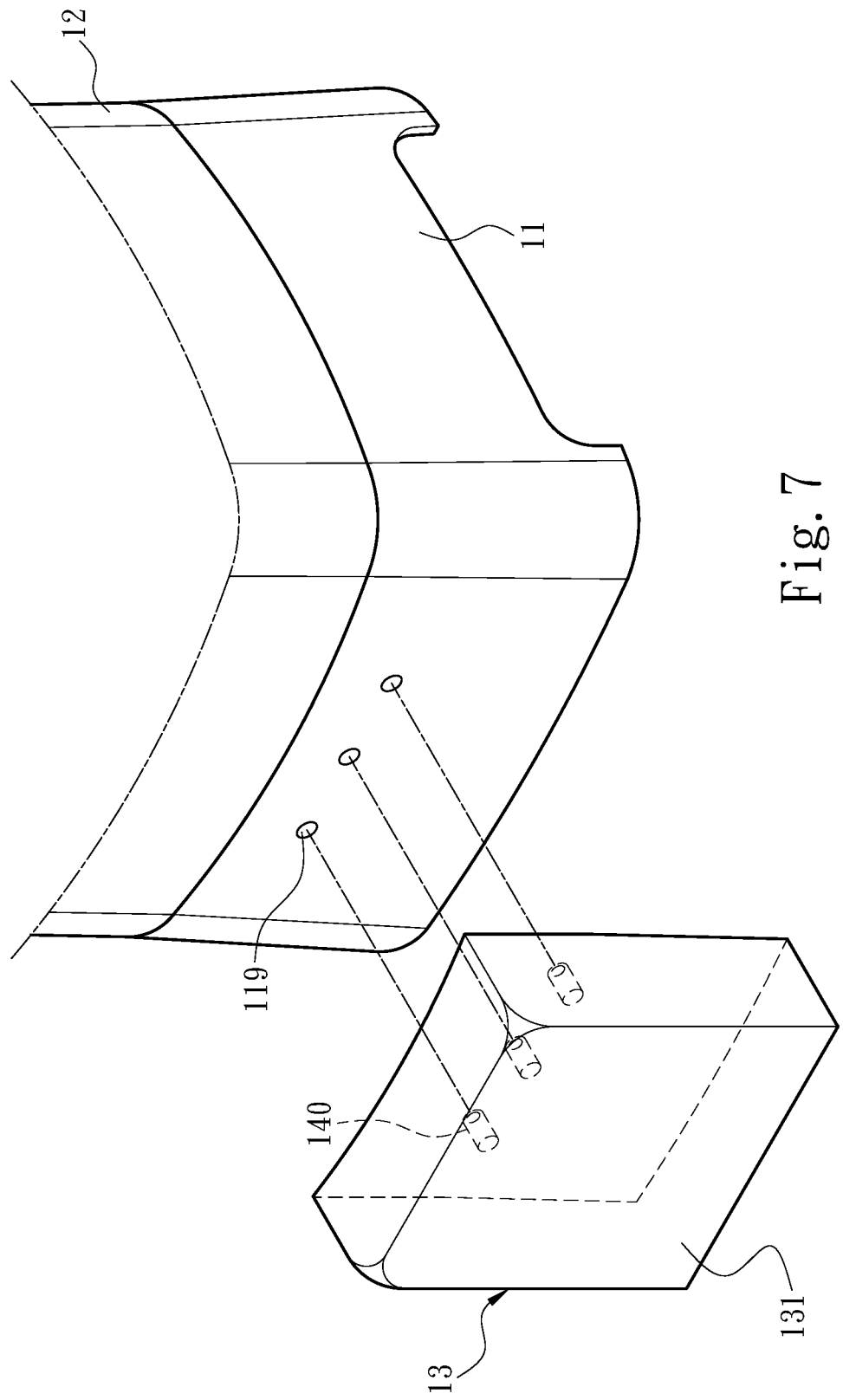
FIG. 7 is a structural exploded view of one embodiment of the present invention.
Figure 8:
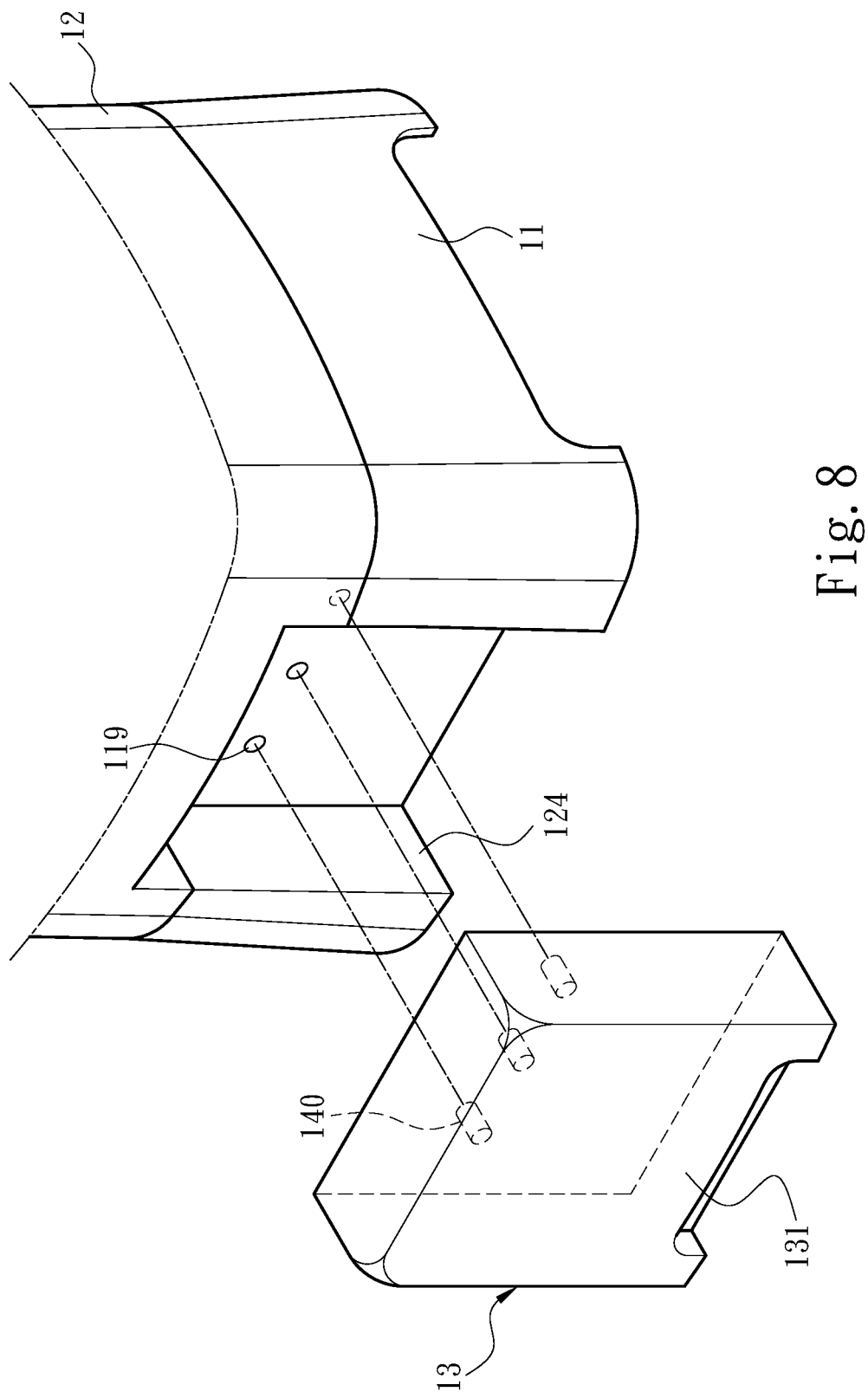
FIG. 8 is a structural disassembled view of another embodiment of the present invention.

Referring to FIG. 7, the essential oil supplier 13 may be dismounted from the main body 11, that is to say, the essential oil supplier 13 may be selectively mounted to the main body 11. When the essential oil supplier 13 is not mounted to the main body 11, humidification of mist is still provided by the humidifier 100. Meanwhile, although water flowed into the temporary liquid storage basin 111 may not be flowed through the essential oil delivering passage 119, one end of the essential oil delivering passage 119 may be closed by means of a plug (not shown in the figure) or a cover (not shown in the figure). Furthermore, referring to FIG. 8, the bucket body 121 in one embodiment includes an accommodating recess 124 provided for the essential oil supplier 13 to be selectively located therein without being prominently projected on the exterior of the water storage bucket 12. Thereby, the essential oil supplier 13 is located within the accommodating recess 124 without being prominently projected on the exterior of the water storage bucket 12, such that the water storage bucket 12 is more aesthetically pleasing in the whole appearance.

Referring to FIG. 1, FIG. 2, FIG. 3, FIG. 4, and FIG. 5 again, the main body 11 includes a plurality of control switches 141 connected to the startup management module 118 and appeared at the outside of the main body 11. Each of the plurality of control switches 141 may be controlled so as to output a control signal to the startup management module 118. Each control signal outputted from each of the plurality of control switch 141 may be defined as an individual control message, such that the startup management module 118 is allowed for performing, after receiving each control signal, a corresponding operation in accordance with the configured control procedure. For instance, one of the plurality of control switches 141 may be used for starting atomization, while another one of the plurality of control switches 141 may be used for supplying essential oil. Additionally, the number of the plurality of control switches 141, configured for supplying essential oil, is not only single one, and may be adjusted on the basis of the essential oil bottles 132. For instance, if three essential oil bottles 132 are allowed to be provided in the essential oil supplier 13, the number of the plurality of control switches 141 is three. In one embodiment, referring to FIG. 1, FIG. 2, FIG. 3 and FIG. 4 again, the main body 11 is provided with a front side 101 having the plurality of control switches 141, and a rear side 102 having the essential oil supplier 13.

What is claimed is:

1. A humidifier with regular addition of fixed quantity of essential oil, said humidifier including a main body and a water storage bucket mounted to said main body, said main body being provided with a temporary liquid storage basin, an atomizing space defined by said temporary liquid storage basin, an atomizing plate located within said temporary liquid storage basin, a projecting stud located within said temporary liquid storage basin, a fan generating air stream within said atomizing space after being started, and a startup management module connected to said fan and said atomizing plate, a high water level line being defined on said temporary liquid storage basin, said water storage bucket being provided with a bucket body, a water supply switch provided on said bucket body and pushed by said projecting stud so as to permit water stored in said water storage bucket to flow into said temporary liquid storage basin, as well as an air guiding passage defined and formed by said bucket body while communicated to said atomizing space without being used for water storage, characterized in that:

said main body is provided with at least one essential oil delivering passage, corresponding to said temporary liquid storage basin, being located higher than said atomizing space and being communicated to said atomizing space, said humidifier being provided with an essential oil supplier mounted to said main body, said essential oil supplier including a casing, at least one essential oil bottle located within said casing and stored with an essential oil, at least one peristaltic pump corresponding to each essential oil bottle and being connected to said startup management module, said peristaltic pump being provided with a pump body, a peristaltic pump head connected to said pump body, and a liquid delivering hose connected to said peristaltic pump head, said liquid delivering hose being provided with a liquid supplying end connected to said essential oil delivering passage, and a liquid drawing end connected to said essential oil bottle.

2. The humidifier with regular addition of fixed quantity of essential oil according to claim 1, characterized in that said casing is provided therein with a supporting panel, said supporting panel being openly provided with at least one mounting hole, said pump body and said peristaltic pump head of said peristaltic pump being located on two sides of said supporting panel, respectively, said pump body being connected to said peristaltic pump head through said mounting hole.

3. The humidifier with regular addition of fixed quantity of essential oil according to claim 1, characterized in that said essential oil supplier is provided with a tube located at the end of said liquid delivering hose to be connected to said essential oil delivering passage.

4. The humidifier with regular addition of fixed quantity of essential oil according to claim 3, characterized in that said bucket body includes an accommodating recess provided for said essential oil supplier to be selectively located therein without being prominently projected on the exterior of said water storage bucket.

5. The humidifier with regular addition of fixed quantity of essential oil according to claim 3, characterized in that said main body includes a plurality of control switches connected to said startup management module and appeared at the outside of said main body.

6. The humidifier with regular addition of fixed quantity of essential oil according to claim 5, characterized in that said main body is provided with a front side having said plurality of control switches, and a rear side having said essential oil supplier.

* * * * *